(12) United States Patent
Funch-Nielsen

(10) Patent No.: US 12,239,430 B2
(45) Date of Patent: Mar. 4, 2025

(54) COLLECTION DEVICE FOR EXHALED BREATH

(71) Applicant: EXHALATION TECHNOLOGY LIMITED, Cambridge (GB)

(72) Inventor: Helle Funch-Nielsen, Horsholm (DK)

(73) Assignee: EXHALATION TECHNOLOGY LIMITED, Cambridge (GB)

( * ) Notice: Subject to any disclaimer, the term of this patent is extended or adjusted under 35 U.S.C. 154(b) by 678 days.

(21) Appl. No.: 17/596,695

(22) PCT Filed: Jun. 19, 2020

(86) PCT No.: PCT/GB2020/051487
§ 371 (c)(1),
(2) Date: Dec. 16, 2021

(87) PCT Pub. No.: WO2020/254819
PCT Pub. Date: Dec. 24, 2020

(65) Prior Publication Data
US 2022/0322962 A1    Oct. 13, 2022

(30) Foreign Application Priority Data
Jun. 19, 2019   (GB) .................................... 1908784

(51) Int. Cl.
*A61B 5/08*      (2006.01)
*A61B 5/097*     (2006.01)
*A61B 10/00*     (2006.01)

(52) U.S. Cl.
CPC .............. *A61B 5/082* (2013.01); *A61B 5/097* (2013.01); *A61B 2010/0087* (2013.01)

(58) Field of Classification Search
CPC . A61B 5/082; A61B 5/097; A61B 2010/0087; G01N 33/497; G01N 2001/2244
See application file for complete search history.

(56) References Cited

U.S. PATENT DOCUMENTS 8,002,712 B2 *   8/2011   Meka ................... G01N 33/497
                                                    600/529
10,238,315 B2 *  3/2019   Smart .................... A61B 5/097
(Continued)

FOREIGN PATENT DOCUMENTS

CA    3056855 A1    9/2018
EP    3027113 A1    6/2016
(Continued)

OTHER PUBLICATIONS

International Search Report and Written Opinion mailed Sep. 14, 2020 in corresponding International Application No. PCT/GB2020/051487.

*Primary Examiner* — Justin N Olamit
(74) *Attorney, Agent, or Firm* — Renner, Otto, Boisselle & Sklar, LLP.

(57) ABSTRACT

The invention as disclosed herein provides a breath-condensate analysis cartridge suitable for incorporation into an exhalation device. The cartridge comprises a condensation zone to receive exhaled breath, the condensation zone having a peripheral region. An analysis chamber is included in which a condensed breath sample is analysed. The surface of the condensation zone acts. to create a fluid flow path in the peripheral region. A fluid flow path through the peripheral region links the condensation zone to the analysis chamber. A lip at least partially covers the peripheral region, the lip co-operating with the condensation zone to form a capillary to control fluid flow.

15 Claims, 20 Drawing Sheets

(56) References Cited

U.S. PATENT DOCUMENTS 11,733,231 B2 *  8/2023  Funch-Nielsen ...... A61B 5/087
                                                73/23.3
12,031,982 B2 *  7/2024  Daniels .................. A61B 5/082

FOREIGN PATENT DOCUMENTS

WO       2010/121072  A1    10/2010
WO       2015/015201  A1     2/2015

* cited by examiner

COLLECTION DEVICE FOR EXHALED BREATH

This application is a national phase of International Application No. PCT/GB2020/051487 filed Jun. 19, 2020, which claims priority to United Kingdom Application No. 1908784.0 filed Jun. 19, 2019, each of which is hereby incorporated herein by reference in its entirety.

FIELD OF THE INVENTION

The invention described herein relates to a microfluidic cartridge, typically of a size similar to a conventional credit card and designed for use in medical diagnostics. The cartridge is specifically for the collection of exhaled breath condensate, and for the immediate analysis of a defined sample volume of the breath condensate within the same cartridge. Within the cartridge the sample is always in contact with one or more surfaces of the cartridge.

BACKGROUND TO THE INVENTION

The present invention is concerned with the collection of exhaled breath, primarily from a human subject, but also from animal, typically mammalian subjects. In a first aspect of the invention a disposable microfluidic cartridge is disclosed which collects and analyses exhaled breath. The cartridge is intended for use incorporated into a larger device which provides a fluid path to receive and direct exhaled breath onto the cartridge, but also has processing functionality to process data determined by the cartridge. Once used, the cartridge can be replaced by a further cartridge, ready to accept another sample.

It is well recognized that analysis of exhaled breath, and especially the alveolar portion of the exhaled breath can provide a good indication of the subject's health. In particular, the presence or absence of certain marker compounds for illness such as hydrogen peroxide, NOx etc. can enable specific medical conditions to be diagnosed or ruled out.

Care needs to be taken however that the sample is obtained correctly, without contamination by including unwanted portions of the breath and also that the sample is obtained without causing the subject, who may already have considerable breathing difficulties, too much distress.

Although microfluidic cartridges are known in the field of breath analysis, they suffer from a number of drawbacks. First the sample size used within the analysis is not always well-controlled. This can lead to errors in results obtained as the volume assumed in any calculation may not be accurate or the deemed concentration of reagents dissolved in the condensed breath may be inaccurate.

Additionally, the size of conventional cartridges leads to less control over the temperature of the analysis, due to the mass of the components and their latent heat capacity being sufficient to influence the analysis temperature. The present invention provides, in a preferred embodiment of the invention, a cartridge of the size of a conventional credit card which is therefore of lower heat capacity and can, particularly where similar materials are used to those utilized in the manufacture of credit cards, also be relatively easily and cost-effectively manufactured being based on conventional technology used in the manufacture of credit cards and the like.

Lightweight disposable, single-use diagnostic strips have been known for many years, and a specific well-known example is the self-monitoring blood glucose strip (SMBG). Such glucose strips are produced in the billions per annum and have a reasonable degree of accuracy, which is currently at about 15%. When manufactured in volume, SMBG strips can cost 2 to 5 cents each to produce. This low cost of production is in part due to the manufacturing volume, and in part to the manufacturing technologies used. The manufacturing techniques can include screen printing, vapour deposition, laser ablation and the lamination of materials to form chambers and channels. It should be noted that SMBG strips are not commonly made from injection moulding, additive or subtractive manufacturing. The substrate used for SMBG strips are typically flexible/semi-flexible polymers upon which thin laminate materials are layered to build a device with microfluidic channels and chambers.

It is therefore an object of the present invention to seek to address the above problems of known breath analyzers.

SUMMARY OF THE INVENTION

According to a first aspect of the invention there is provided a breath-condensate analysis cartridge suitable for incorporation into an exhalation device, the cartridge comprising;
- a condensation zone to receive exhaled breath, the condensation zone having a peripheral region;
- an analysis chamber in which a sample is analyzed;
- the surface of the condensation zone acting to create a fluid flow path in the peripheral region;
- the condensation zone being linked to the analysis chamber by a fluid flow path through the peripheral region;
- a lip to at least partially cover the peripheral region, the lip co-operating with the condensation zone to form a capillary to control fluid flow.

Preferably the condensation zone is circular and further preferably has a diameter of from 15.0-25.0 mm and yet further preferably of 20.0 mm.

The surface of the condensation zone is preferably coated or formed of a hydrophilic material which enables the condensed fluid to form a film across the surface.

The hydrophilicity of the surface of the condensation zone is preferably selected to be such as to form an angle with breath condensate of less than 20.0° and further preferably from 5.0°-15.0°. This allows the breath condensate to run freely off the condensation zone and into the sensing zone.

Alternatively, the sensing zone includes an air-vent and the hydrophilicity of the surface of the condensation zone is optionally selected to be such as to form an angle with breath condensate of less than 23.0°-35.0° and further optionally from 24.0°-26.0°. This allows aa critical mass of condensate to be formed which then runs in to the sensing zone as a combined mass.

Preferably, the lip includes a narrow strip whose first end is adjacent or contiguous the analysis chamber. The width of the strip is preferably from 125-400 µm, and particularly preferably 125-300 µm.

The distance of the strip from the condensation zone is preferably from 125-350 µm and especially preferably from 250-300 µm.

Optionally, a portion of the condensation zone is formed of or coated with a hydrophobic material, the portion being located adjacent the analysis chamber and the peripheral region.

Conveniently the overall dimensions of the cartridge are that of a conventional credit card.

Optionally, the cartridge has a laminar structure which aids in allowing the cartridge to bend and hence be more flexible than a conventional cartridge utilized in the art.

BRIEF DESCRIPTION OF THE DRAWINGS

The invention is now described with reference to the accompanying drawings which show by way of example only, 2 embodiments of a cartridge. In the drawings.

DETAILED DESCRIPTION OF THE INVENTION

Figure 1:
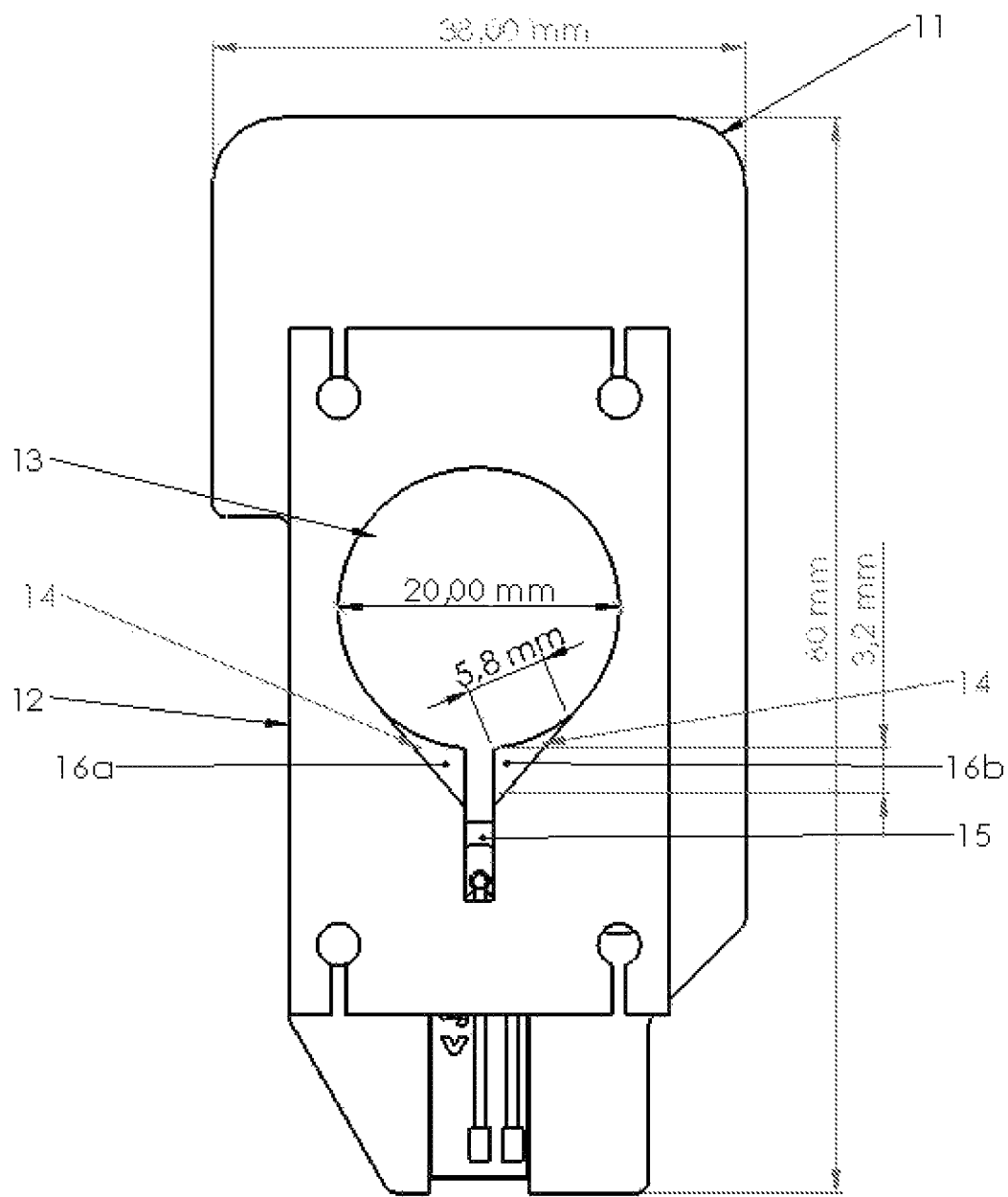
FIG. 1 illustrates component parts of a first embodiment of a cartridge.

The present invention aims to provide a cartridge for use in a device for analyzing breath condensate. Incorporated into the cartridge is a coolable collection zone in which exhaled breath is collected. The collection zone is fluidly connected to one or more analysis regions in which, usually, a defined volume of the collected breath is mixed with reagents and then analyzed to determine the presence of and/or concentration of the required analyte. The device into which the cartridge is incorporated can be provided with functionality such as to identify when a sample has entered the cartridge, when sufficient sample has been collected, processors to carry out calculations on a signal from the cartridge relating to an assay being carried out and communication means to transmit a reading or result to a device-mounted display or remote display.

The cartridge described within this document is designed to fit within a reader device. Within the device, the collection zone is brought into cooling engagement with a thermal sink such as a Peltier cooler mounted within the device. All processes are performed within the cartridge including: the cooling of the breath sample, the condensation of a breath sample as a film on a condensing zone, the processing of the sample and the final analysis. The condensing zone has a hydrophilic surface which assists the movement of the sample from a collection zone to a sensing zone under the influence of gravity and avoids the formation of droplets.

The cartridge has two principal zones within it: the collection zone and the sensing zone. The condensing zone of the collection zone is where the exhaled breath is condensed whilst the sensing zone, which is highly integrated with the collection zone, is where the analyte detection and quantification takes place. The detection and quantification of the analyte(s) can take place by a number of analytical techniques, including: UV-Vis spectroscopy, fluorescence spectroscopy, surface plasmon resonance, impedance spectroscopy or electro-analytical chemistry. In the case of techniques including electroanalytical chemistry and impedance spectroscopy it is necessary to have electrodes within the sensing zone. These electrodes can be made by a number of techniques including adhesion of conductive foils, vapour deposition, thick film printing etc. These electrodes can be applied directly onto the substrate that forms the 'base' of the cartridge or can be printed on a second material that is then slotted into the 'base' of the cartridge.

The cartridge is preferably provided in a credit card format and size, which offers advantages both from a user perspective and a manufacturing cost perspective, as a credit card has a size and shape that is familiar and optimum for handling by a large proportion of the population, and also offers a platform conducive to large scale and low-cost manufacturing. Credit cards conform to ISO/IEC 7810 and are manufactured in the billions per year so have a very optimized cost structure as the supply chain is highly developed and matured.

Similarly to the SMBG strips described above, a cartridge described within this patent can be made by a printing and lamination process but, unlike the SMBG strip, is provided in credit card format. The use of such a process allows softer materials to be used, reducing the tolerances to which the cartridge can be manufactured. Moreover, the softer materials provide compressibility and the laminar structure the capacity for the cartridge to bend, enabling the cartridge to be fitted into the device more easily.

The cartridge has several functionalities, including the collection of exhaled breath condensate. The need to condense and collect breath requires a phase change of the sample and this imposes requirements on the cartridge not encountered in prior art disposables designed for medical diagnostic applications. One such requirement imposed by the application is the need for a large surface area for exhaled breath collection. The amount of exhaled breath that can be collected per second is proportional to the surface area of the condensation zone. If the cartridge were small, with dimensions similar to an SMBG strip, typically 7 mm×20 mm, then there would not be a sufficient area to collect the patient's breath within a reasonable time. The use of a credit card format in the present invention allows for a circular breath collection zone with a diameter of approximately 20.0 mm, although diameters of from 15.0-25.0 mm can be considered. This provides a large surface area for condensation, but which can be cooled and upon which the patient's breath can be collected.

Within this invention sufficient patient's breath can be collected within 60 seconds. Prior art exhaled breath condensation collectors, positioned for the medical and medical research market, require that the patients breathe for some minutes in order to collect an adequate volume of sample. This is unacceptable for many clinical applications and patient groups. If one considers patients with asthma, chronic pulmonary obstruction disease, cystic fibrosis etc. then these types of patients can have difficulties breathing and so the requirement of other breath collection cartridges/devices to have the patient breathe for some minutes is both unethical and can influence the results of any downstream assay.

The cartridge described here is optimized to reduce the stress upon the patients, as the resistance to exhaled breath is minimized, and the large collection area and small sample volume required reduces the necessary duration of breathing into the device. Therefore, the patient provides quickly an exhaled breath condensate sample on the cartridge whilst carrying out only normal tidal breathing.

Along with the large condensation surface the cartridge also provides an additional benefit to the patients because of the microfluidic features, channels and chambers incorporated in the device. Traditional exhaled breath condensate collection devices collect some 100s of microlitres to some millilitres of sample. This volume requirement by the prior art devices means that no matter how efficient the condensation of the breath it takes a certain amount of time to condense 100 microlitres or more of exhaled breath condensate. The cartridge discussed here has a sensing volume of 4 microlitres and this reduction in the actual volume of sample required means that sample collection time is considerably reduced. The volume of the condensing zone relative to the sensing zone is approximately 10:1 which further aids in the rapid collection of sufficient volume.

The device described herein further reduces the sample required to be condensed because the condensing zone is provided with a hydrophilic surface. The advantage of a hydrophilic surface is that droplets do not form on the surface of the condensing zone. The issue with droplet formation is that droplets are typically 10 microlitres or more in volume. Therefore, a hydrophobic surface that promotes droplet formation has the consequence of the patient needing to provide approximately 10 microlitres of volume before a droplet is formed. These droplets then 'sit' on the surface until their mass is sufficient to overcome any hydrophobic forces and they can begin to flow. The use of a hydrophilic surface causes a film of condensate to form on the surface rather than in droplets, and the film is able to start flowing very quickly after the breath is first condensed.

When in collection mode the cartridge is preferably held in the vertical plane and gravity is enough to move the sample from the collection zone downwards towards the sensing zone. The movement of the exhaled breath condensate film is not random, rather the sample tends towards the edges where a lip around the circumference of the collection zone provides, in combination with the walls and condensation surface of the condensation zone, a capillary channel that routes the sample. The sample after moving initially downwards under gravity, follows along the edge of the collection zone, before entering a capillary chamber at what is the lowest point of the collection zone when the cartridge is in this orientation. This second chamber is referred to as the sensing zone/chamber. This chamber is closed around its sides, typically four in number, by cut laminate, with a top cover providing the lid of the chamber. The sensing zone is effectively bounded but open to the collection zone. The chamber is also held in the vertical plane when in collection mode and whilst the patient is breathing into the device.

Some exhaled breath condensation devices described elsewhere have the collection zone positioned in the vertical plane, but have the sensor in a horizontal plane, where the sample drips from one surface to another. This configuration has the disadvantage that in order to move as a drop from one surface to another the drop has to have a critical mass: in order to form the drop and for the drop to break away from the surface. Again, the collection and sensing zones within the cartridge having a credit card format and being in the same plane allow the exhaled breath condensate film to run easily from the collection zone to the sensing zone. The sample is guided into the sensing zone along the walls of the edges of the capillary channel formed at the edge of the condensation zone.

The sensing zone in this embodiment fills from the bottom up, because the sample flows down the sides of the chamber before then filling from the bottom up. This is a departure from SMBG strips where the sample is often encouraged to fill a capillary tube in an even way and to fill from the front of the capillary, effectively pushing a front of trapped air in front of the liquid sample. SMBG strips often have an air vent to give the trapped air an escape route. The issue of trapped air is avoided in this embodiment of credit card device as the liquid sample is guided down the walls to the bottom of the chamber, filling the chamber from the bottom, which process is aided by the vertical placement of the cartridge during the collection of the sample.

Within this sensing chamber reagents can be added to the sample. In order to make an electrochemical measurement upon a sample it is prudent to control several parameters including pH and conductivity, and so within the chamber dried reagents are provided for buffering and adding electrolytes. Further in order to have specificity it is necessary to have an assay within the chamber designed to measure the analyte or parameter of interest. In the case of analytes such as nitric oxide, pH, hydrogen peroxide etc. there is often an assay which has been designed to give specific signal.

As described above, the assay may require the addition of reagents to the sample volume, and therefore the capacity to control the fluid volume is even more important as the additional reagents need to subsequently disperse to give a pre-determined concentration. For example, in many in vitro diagnostic assays (IVDS), optically or electrochemically active materials are added to the sample. The concentration of these species can affect the final measured values, impacting both the precision and accuracy of the assay. The mass of these materials included in an assay is controlled firstly through the manufacturing process, for example the controlled deposition of a known mass of material into a chamber or well, but the final concentration within the sample is dependent upon the volume of the sample into which a material disperses and/or dissolves. A difference in a sample volume affects the concentration of the added material within that sample, and variation in volume subsequently affects the accuracy of the assay results.

The control of volume can be achieved using fixed volume chambers, pumps and valves etc., and though some of these macro-world solutions work well for volumes greater than a millilitre, they can be less effective for microlitre scale volumes, where surface interactions are more significant relative to bulk properties. In accordance with the herein described invention is a cartridge that fills under the influence of gravity and in which the sample enters a fixed volume chamber. The microfluidic cartridge has features such that once the chamber is filled to the correct volume then no more liquid enters the chamber, but rather excess fluid is held outside the chamber, with a very small contact point between the sample inside the chamber and the sample outside the chamber. This small contact point acts as a choke point with the result that there is very little mass or heat exchange between the fluid inside the chamber and fluid outside the chamber.

In one embodiment of the device is provided a collection zone, where a vapour sample, such as breath, is condensed, and due to the hydrophilicity of the surface on which condensation occurs, the sample runs under the force of gravity down the collection zone as a continuous film into the sensing zone. The inclusion of a partial lid around the edge of the collection zone creates a channel which the moving film of sample prefers to follow. The flowing film moves into a chamber of the sensing zone; the solution flows down the sides of the chamber 'clinging' to the sides of the chamber by surface tension, and effectively filling the chamber from the bottom up in a continuous fashion. In scenarios where fluid continues to flow the chamber could be predicted to overflow, with the overflow remaining in direct contact with the sample, leading to an unclear total volume. In the design described herein the overflow is prevented from freely contacting with the sample within the chamber by one or more capillary sinks. Before the filling of the chamber the sinks are part of guiding the fluid sample to the chamber, but upon filling the pressure of the now-filled chamber, prevents further fluid entering the chamber. Rather than the fluidic overflowing and building up directly on top of the chamber, the overflow is partitioned into capillary sinks and any additional sample is retained within the capillary overflow sinks.

Moreover, the interface between the collection zone is structured and/or formed of a material such that the wetted contact between the overflow sinks and the chamber containing the sample has a surface area of less than 0.2 mm$^2$, and therefore it offers a very small interface between the sample within the chamber and the sample overflowing and captured within the capillary overflow sinks. In a situation where reagents are added passively or actively within the sensing chamber then the volume of sample into which they dissolve is controlled by the dimensions of the chamber, whilst the otherwise unknown sample volume overflow is only in contact with the sample through the small interface so ensuring a more accurate control of the concentration of materials added to the sample within the chamber.

The interface can have a form such as a structure in the form of a capillary tube or the like. Alternatively or additionally, the surfaces of the collection zone and the sensing zone can be formed of a hydrophobic material except for a hydrophilic strip or channel linking the volume within the chamber to the overflow sample outside the chamber. The excess sample can be further encouraged to remain outside the chamber by capillary structures providing surface area for the sample to adsorb to, so providing energy gain sufficient to prevent the sample from running or attempting to run back into the sensing chamber.

This invention provides an elegant control initially of the volume of sample within the sensing chamber and subsequently the concentration of any materials passively or actively added to the sample within the chamber. The final sensed volume of the sample is controlled, and any excess sample is stored outside the sensing chamber. The result is that any materials added to the sample within the sensing chamber, to improve analysis, can dissolve and disperse to give a controlled final concentration.

The use of a main, capillary-controlled, chamber for the sample coupled to overflow sink capillary chambers gives a control of the sample volume without the need for fluid level sensing, active valving and/or pumping etc.

With specific reference to the Figures, FIG. 1 illustrates the internal working features of a cartridge in accordance with a first embodiment of the invention. The overall outer dimensions of the cartridge 10 are similar to the dimensions of the base layer 11 which has a width of around 38 mm and a length of around 80 mm.

Overlaid on this is an analysis layer 12. The analysis layer 12 includes a condensation zone 13, of around 20 mm in diameter, which is exposed along the majority of its surface and in use is fluidly connected to a mouthpiece (not shown) of the device and so receives exhaled breath from the user, which breath condenses to a fluid in the condensation zone 13. The surface of the condensation zone 13 is formed of or coated with a hydrophilic material which causes the condensed breath to spread out as a film across its surface. In the first embodiment the material has a hydrophilicity such that the contact angle between the condensed fluid and the material is less than 20.0° and preferably 5.0-15.0°. The film structure acts to cause fluid to flow downwards along the edge of the condensation zone 13 towards the analysis chamber 15, when the cartridge 10 is held such that the analysis region is lowermost.

It is important, as set out previously, that the volume of fluid within the analysis chamber 15 be a well-defined volume. Therefore, in order to ensure the correct volume is achieved, once the correct volume is reached, then further inflow of or mixing with fluid still in the condensation zone 13 is minimized.

Figure 2:
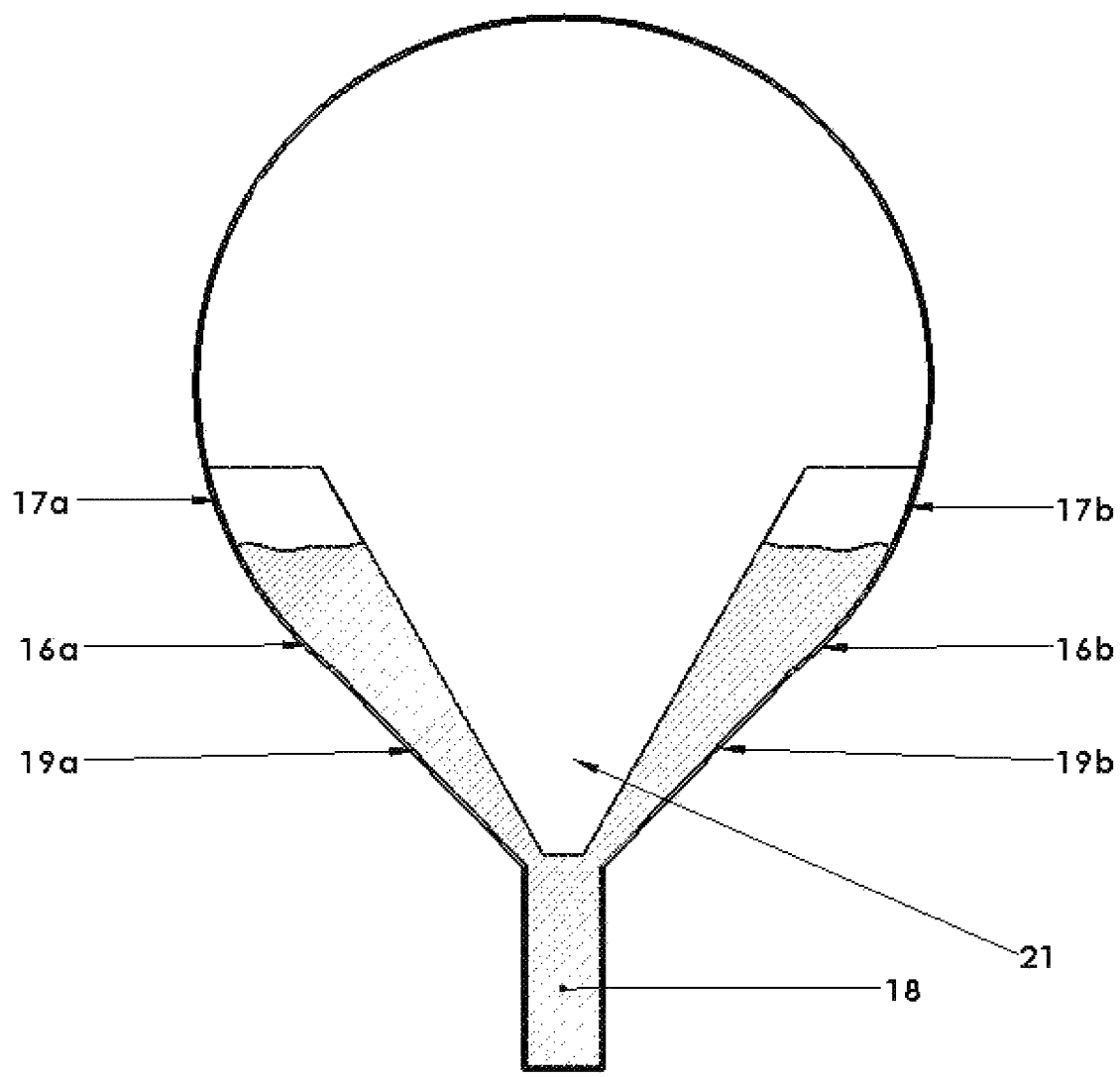
FIG. 2 illustrates fluid retained around the periphery of a condensation zone.

To this end, lips 16a, 16b are provided above and parallel with the surface of the condensation zone 13 in the region of the edges 14 of the condensation zone 13. The lips 16a, 16b are illustrated in FIG. 2. As can be seen in the embodiment of FIG. 2, the lips 16a, 16b have a section 17a, 17b of broader width than a narrow strip 19a, 19b, each having a second end terminating adjacent the analysis chamber 15. Contact with or flow into of fluid in the analysis chamber 15 by fluid not required for the analysis is thereby restricted. The analysis chamber 15 is covered by a roof 18 which, together with the base and walls of the analysis chamber 15 provides the correct volume required for the fluid in the analysis chamber 15.

Preferably, the lip includes a narrow strip whose second end is adjacent or contiguous the analysis chamber, has a width of preferably from 125-400 μm, and particularly preferably 125-300 μm.

Figure 3A:
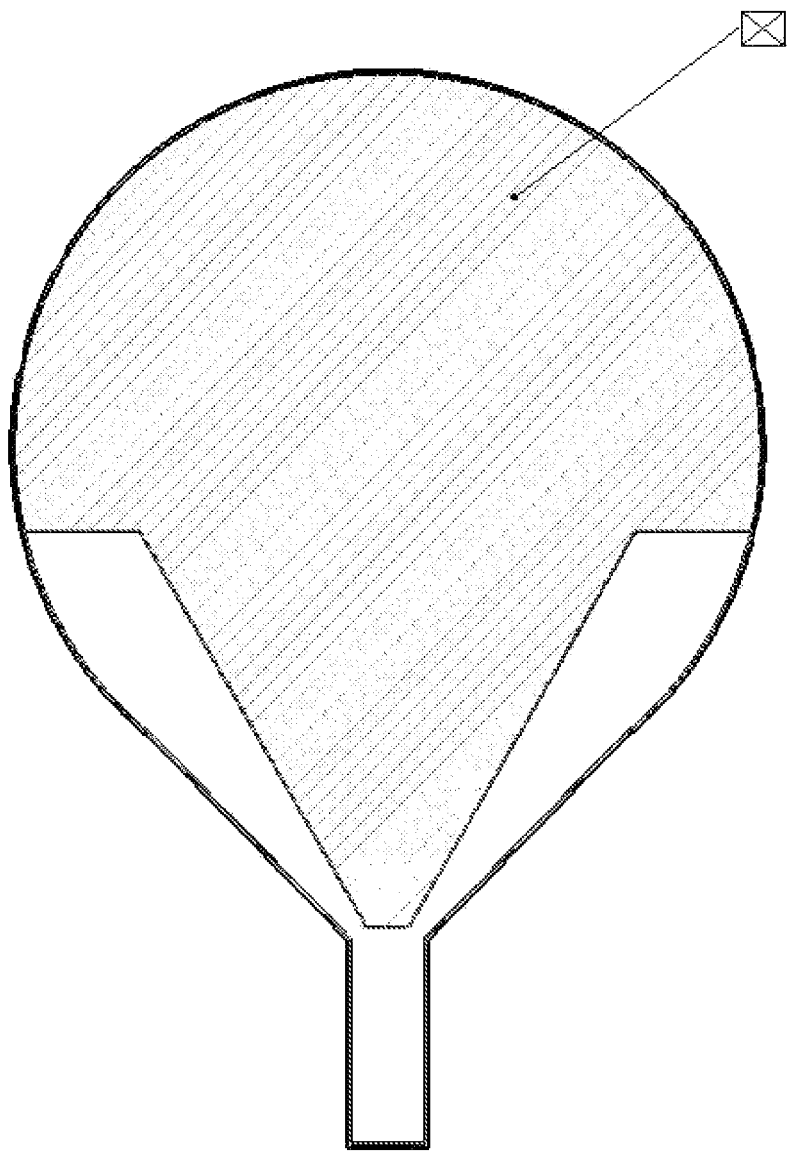
FIGS. 3a-3c illustrate fluid flow in a cartridge.
Figure 3B:
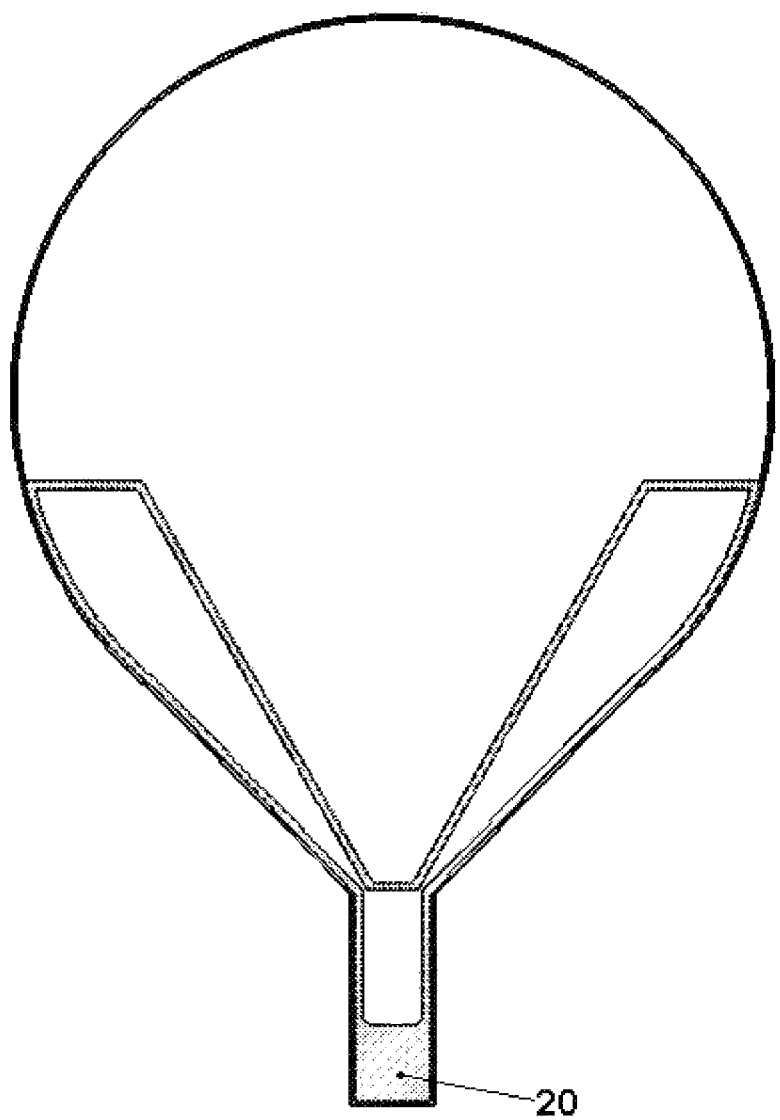
Figure 3C:
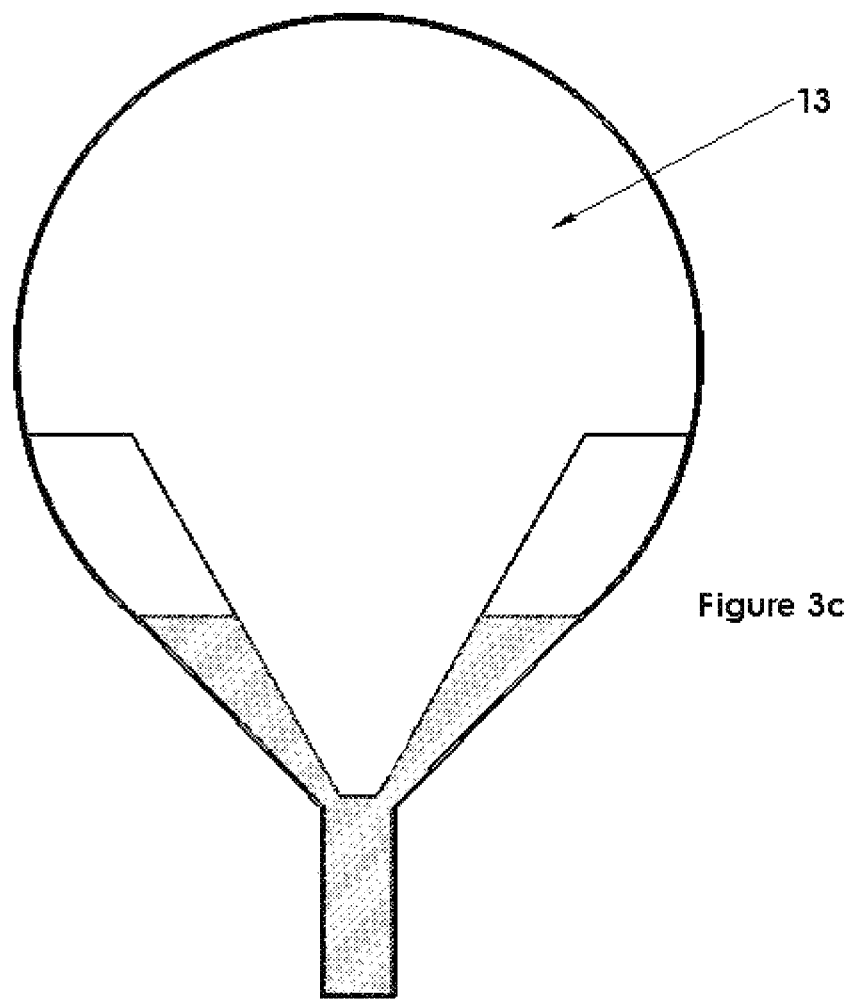

As is summarized in FIGS. 3a-3c fluid condenses in the condensation zone 13. The condensed fluid flows around the edge of the condensation zone 13 and into the lower region 20 of the analysis chamber 15. Flow continues until the required amount of fluid is in the analysis chamber 15. Further fluid is then confined beneath the structure of the lips 16a, 16b. The confinement is assisted by, in an optional embodiment, a hydrophobic region 21 of the condensation zone 13 separating the surface beneath the lips 16a, 16b and which region 21 of the condensation zone 13 is formed of or coated with a hydrophobic material.

Figure 4A:
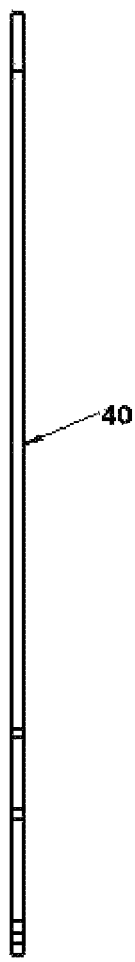
FIGS. 4a-4c are, respectively a side view, plan view and perspective view of a base card.
Figure 4B:
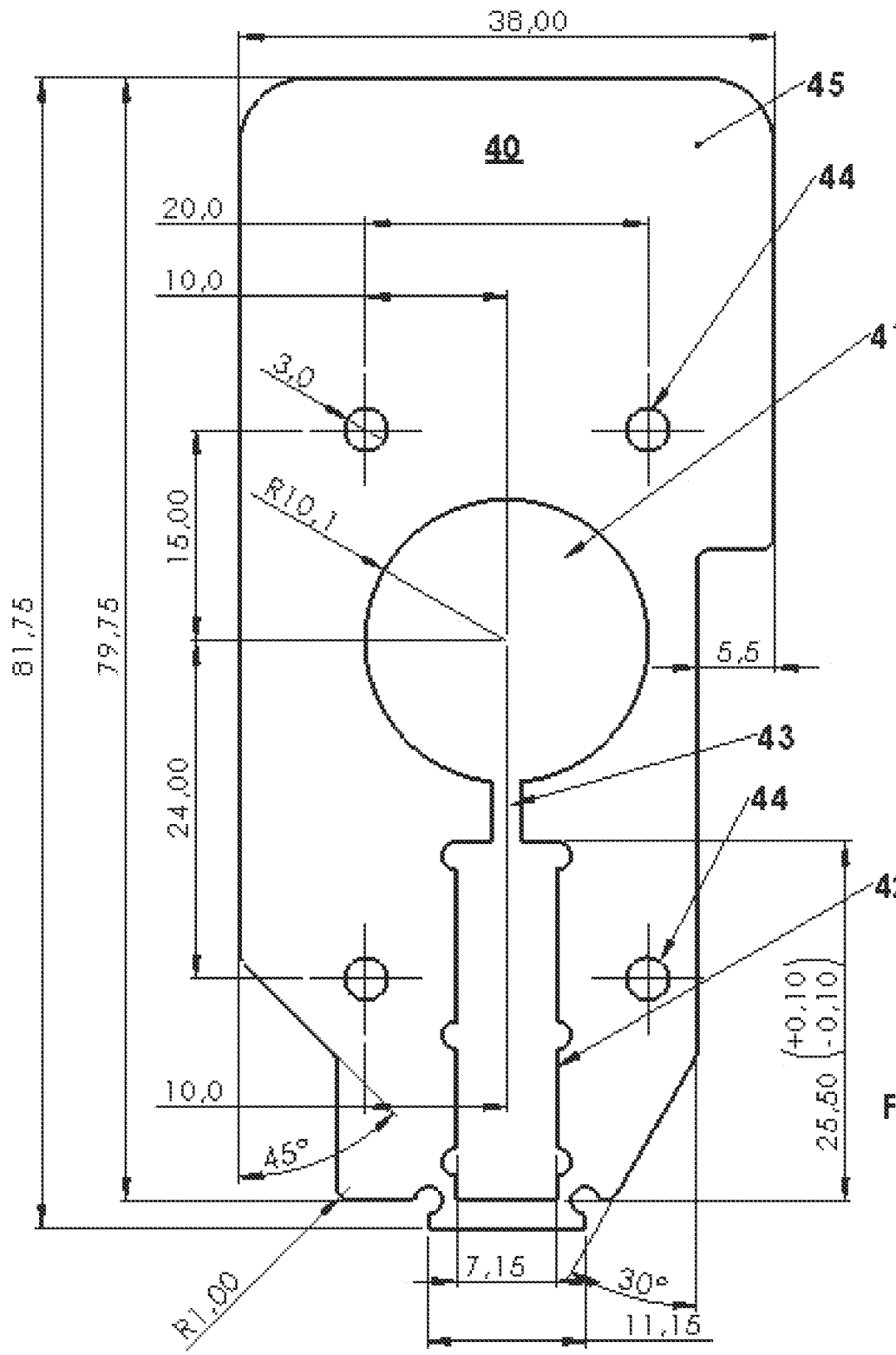
Figure 4C:
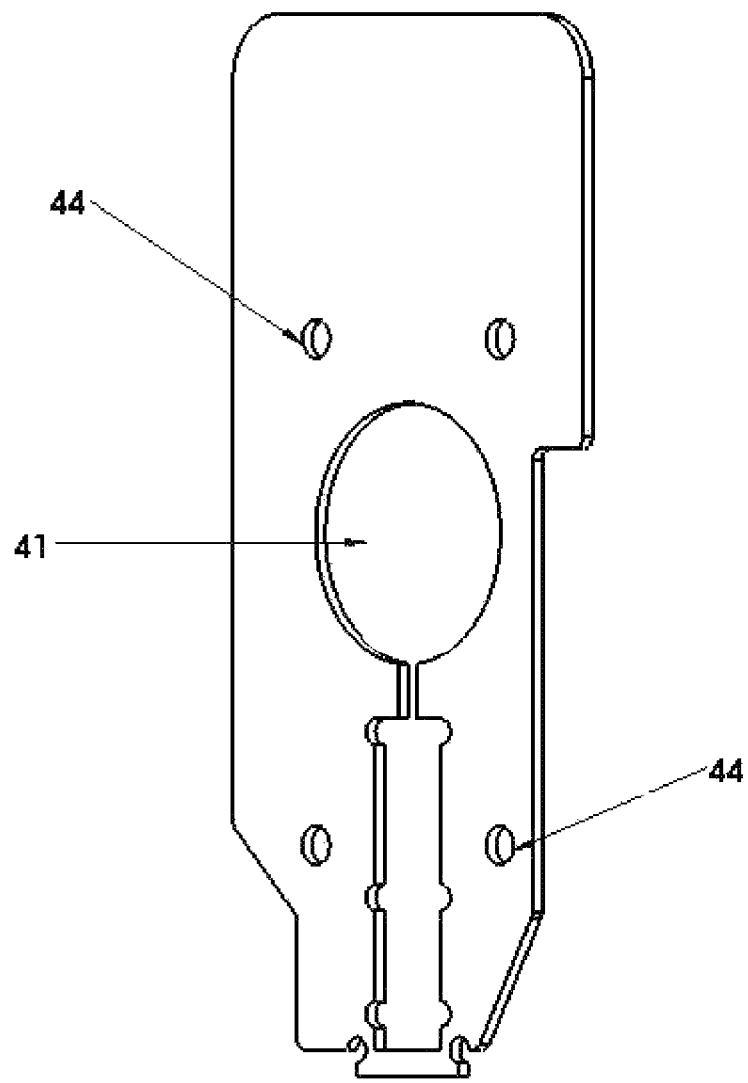

Reference is now made to FIGS. 4-8 which illustrate the assembly of a cartridge in accordance with an embodiment of the invention. The cartridge assembled has a laminar structure formed of multiple layers held together by means known in the art. The laminar structure provides flexibility and strength to the cartridge, which is important generally, but also for example where the cartridge may be being used in an agricultural environment, where conditions are not as well controlled as in a medical environment. In FIG. 4 is illustrated a base card 40 to support other elements of a cartridge. The base card 40 is generally rectangular and has a number of cut-outs and apertures to accommodate the working elements of the cartridge.

The base card 40 has an approximately circular central aperture 41, which in the exemplified embodiment has a radius of 10.5 mm. The walls of the aperture form part of the rim of the condensation zone. A further aperture 42 is so shaped to accommodate the sensing zone, including the analysis region. A channel 43, 2.0 mm in width links the central aperture 41 with the further aperture 42 to allow fluid to flow between the collection zone and the sensing zone and to receive, in some embodiments, a sensor card comprising reagents, electrodes etc. for carrying out the analysis. Apertures 44, of radius 3.0 mm allow the base card 40 to be secured to the other elements of the cartridge by known securing means.

In use, the base card 40 is secured to a main body of the device into which the base card 40 is to be incorporated. The device is provided with a fluid pathway, one end of which receives breath from the user. The second end of the fluid pathway is aligned with the aperture 42 to admit exhaled breath or a component thereof.

Figure 5A:
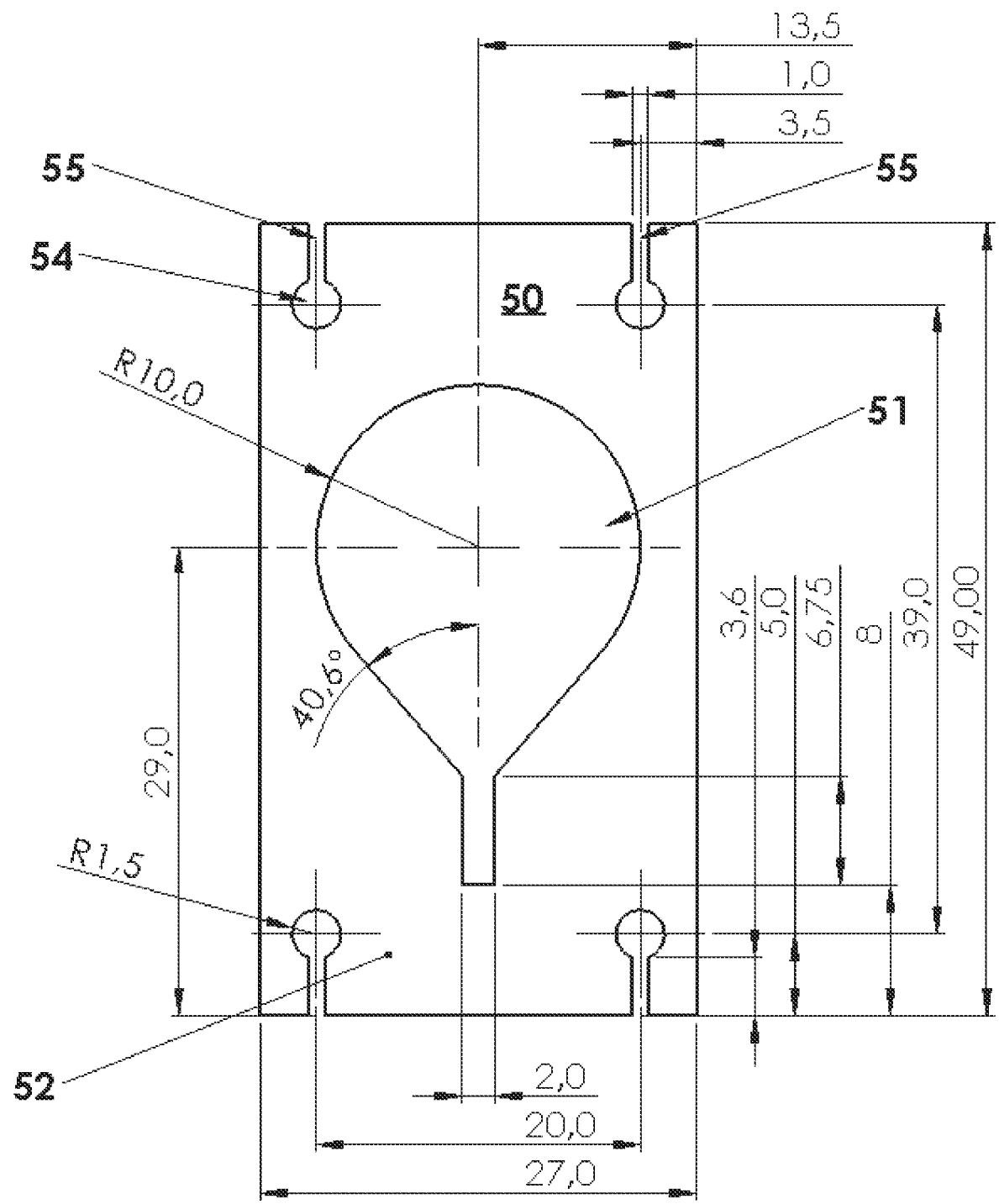
FIGS. 5a, 5b are, respectively, a plan view and perspective view of a cover sheet.
Figure 5B:
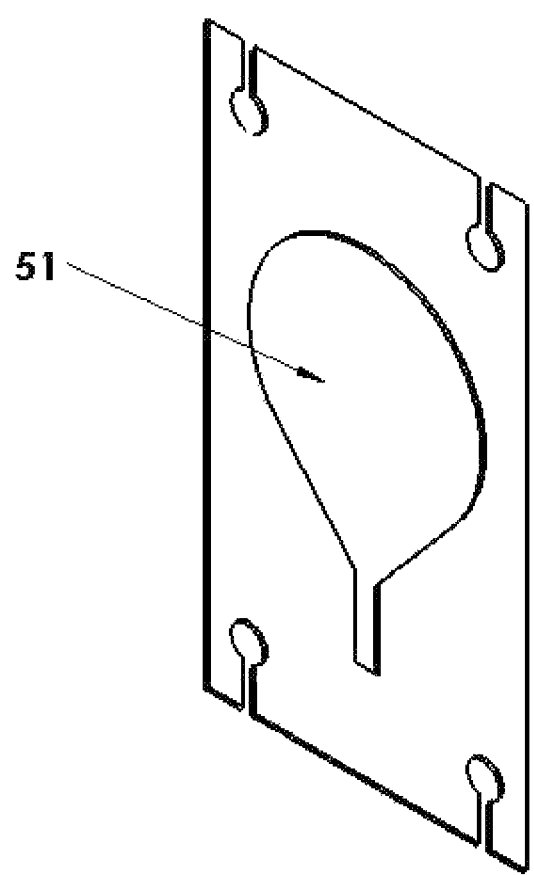
Figure 6A:
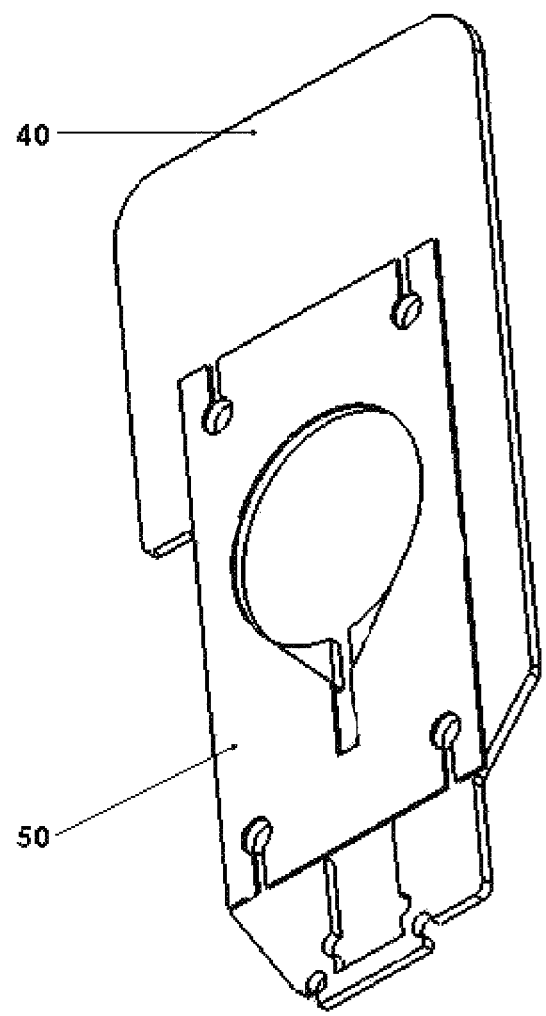
FIGS. 6a, 6b are, respectively, a perspective view and a plan view of the assembled base card and cover sheet of FIGS. 4 and 5.
Figure 6B:
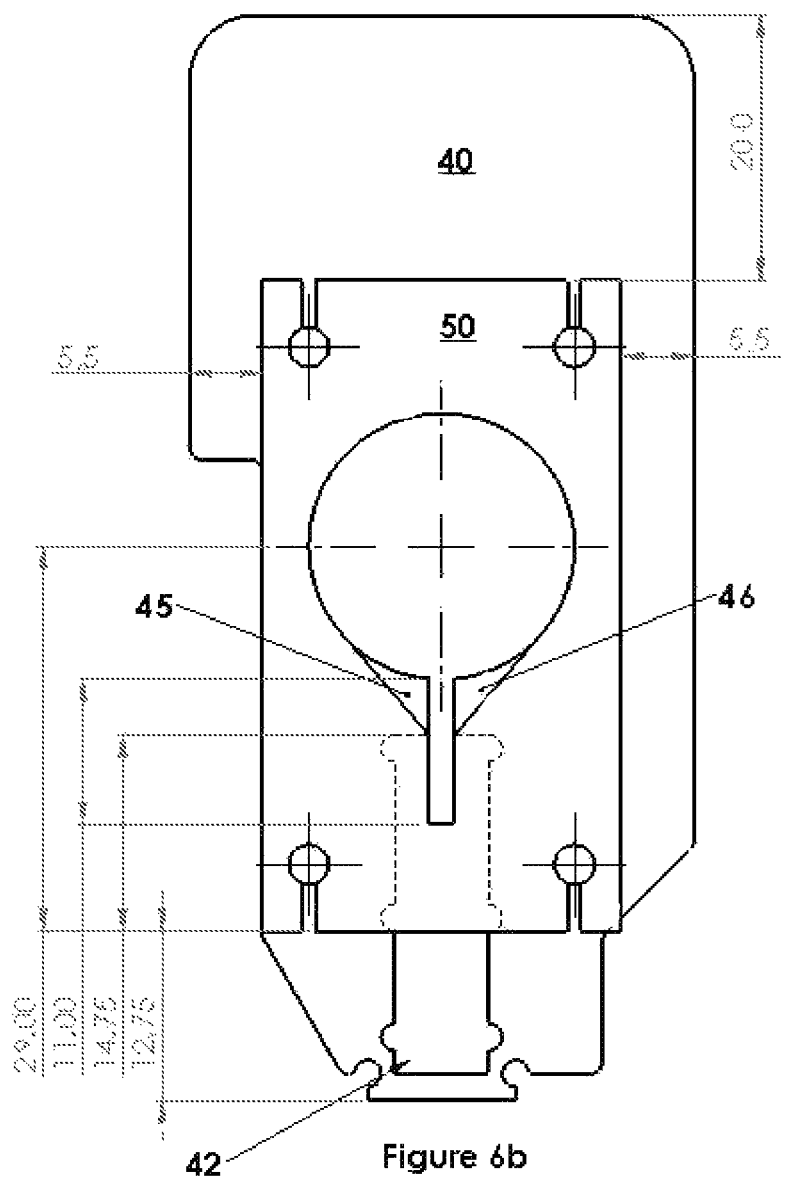

FIGS. 5*a*, 5*b* show a first cover sheet 50 which in use sits over, and is secured to, the surface 45 of the base card 40. Similarly to the base card 40, the first cover sheet 50 has a central aperture 51, which forms, in use, the wall of a condenser plate. The central aperture 51 has a teardrop shape but has a substantially circular portion whose radius matches that of the central aperture 41. Apertures 54 enable the cover sheet 50 to be secured in position, with the channels 55 allowing the cover sheet 50 to be slid about any screws, pins or other fixing means which may be in position.

Figure 7A:
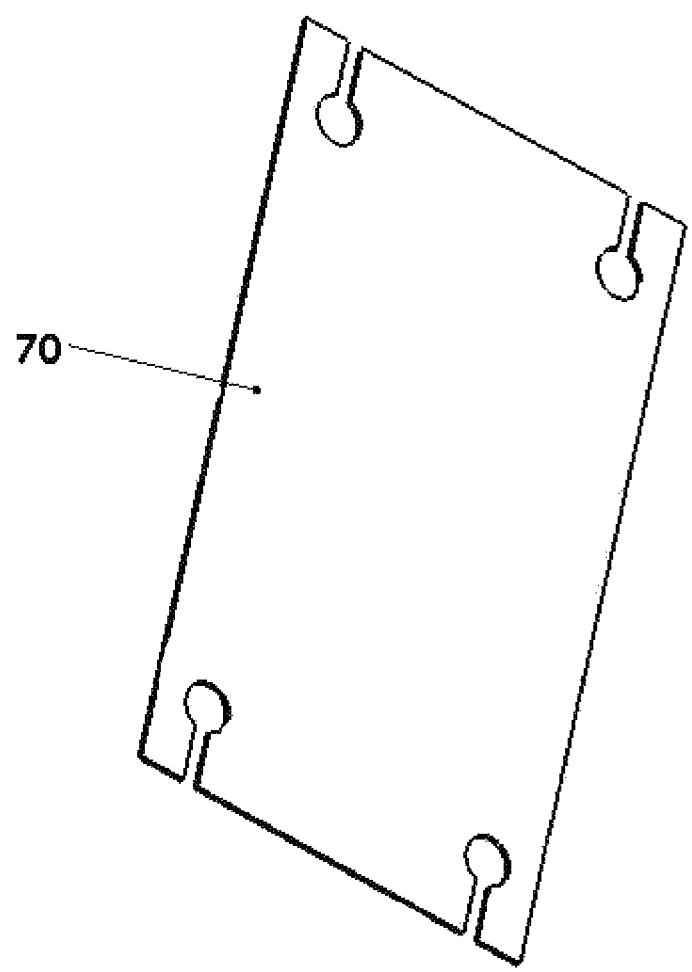
FIGS. 7a, 7b are, respectively, a perspective view and a plan view of a cover plate.
Figure 7B:
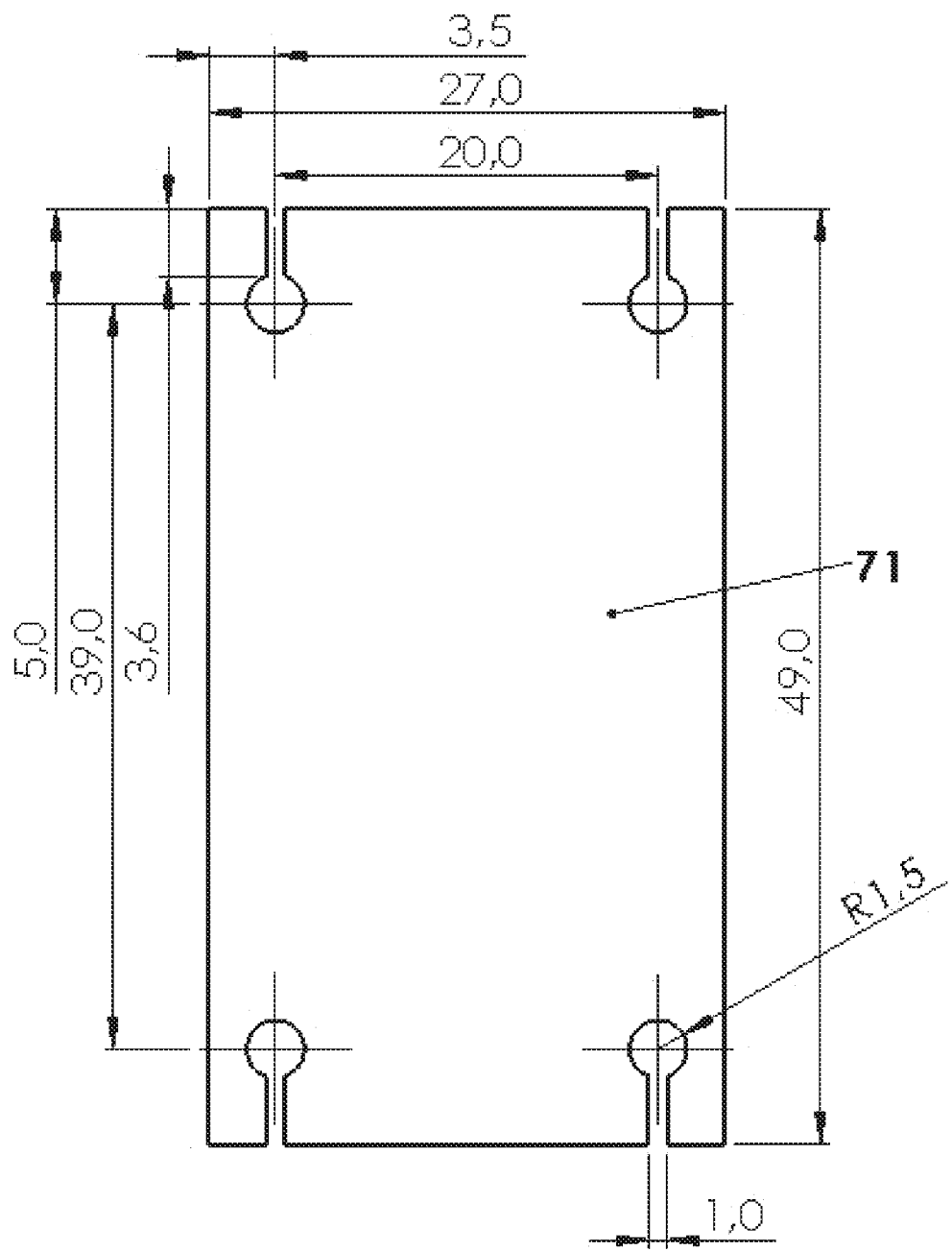
Figure 8A:
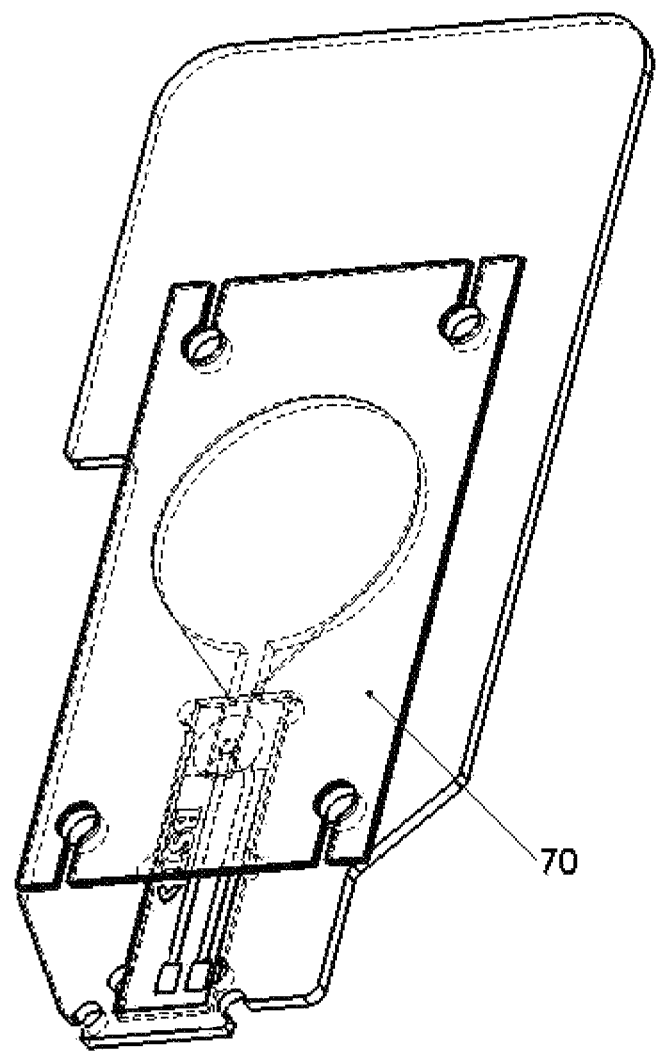
FIGS. 8a, 8b are, respectively, a perspective view and a plan view of the assembled elements of FIGS. 4 to 7.
Figure 8B:
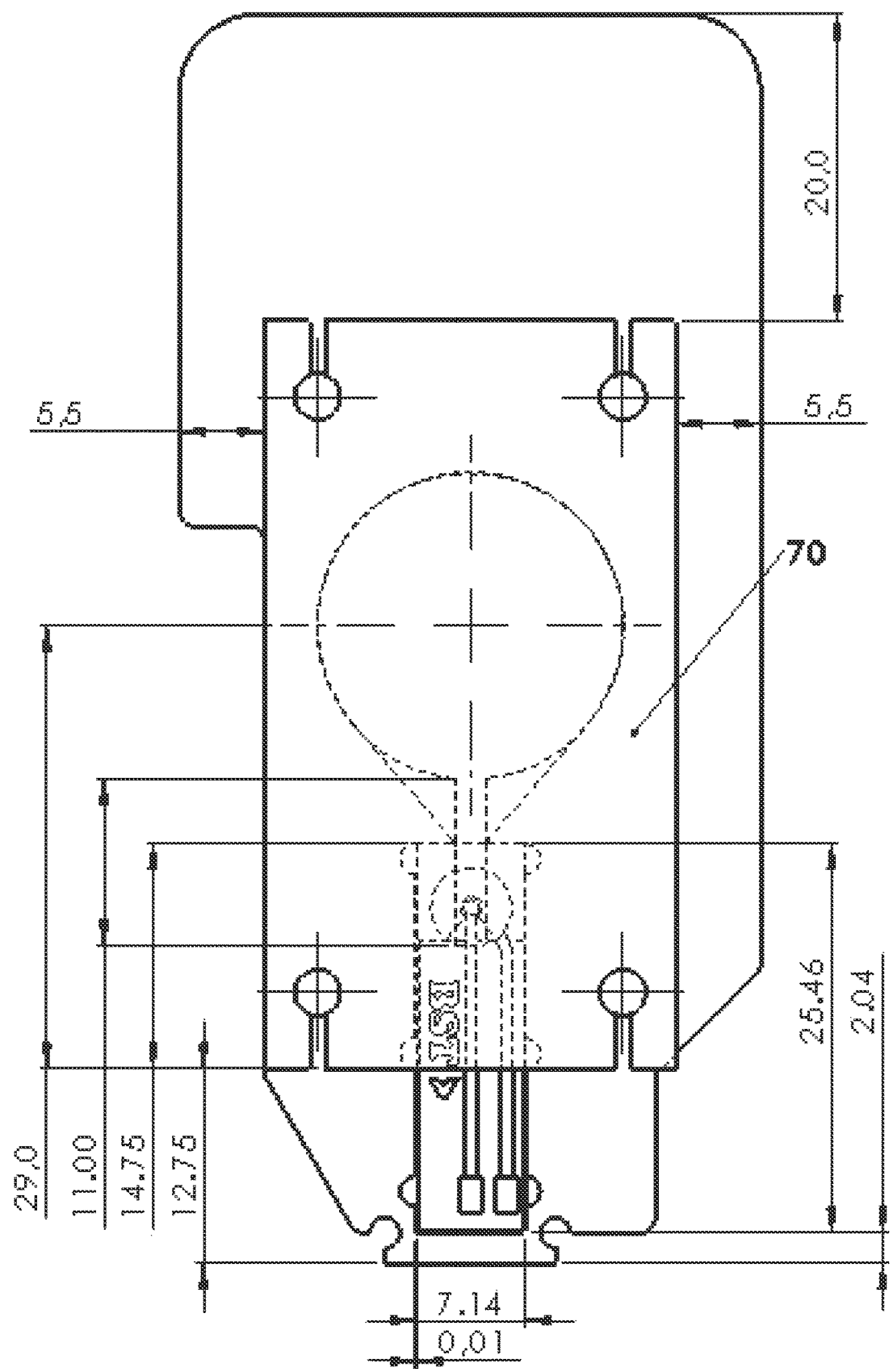
Figure 9:
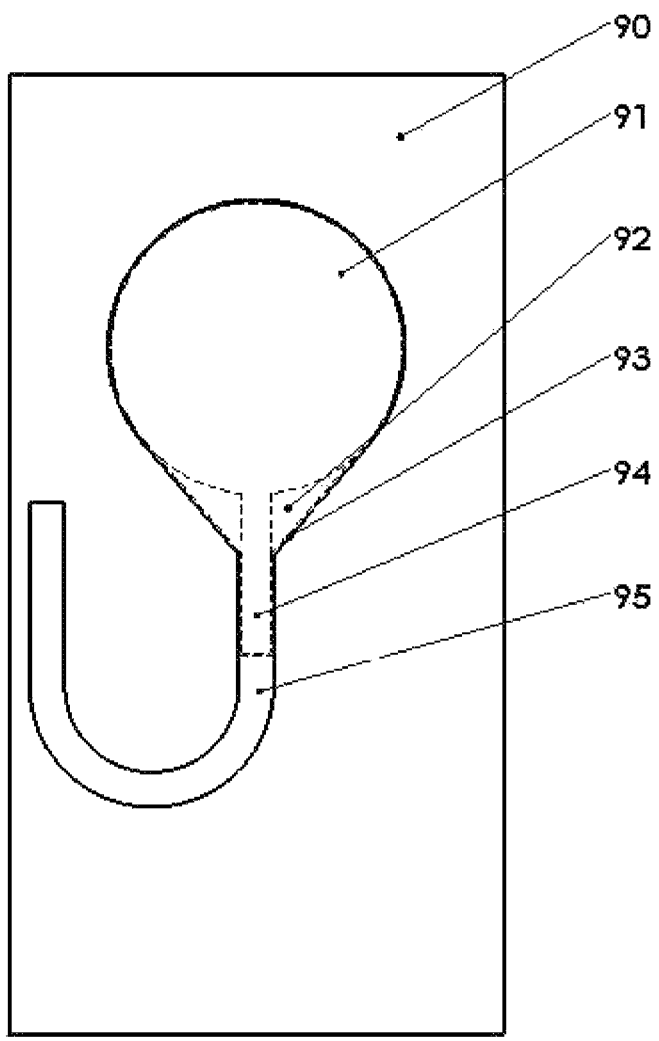
FIGS. 9-12 illustrate the action of a second embodiment of a cartridge.
Figure 10:
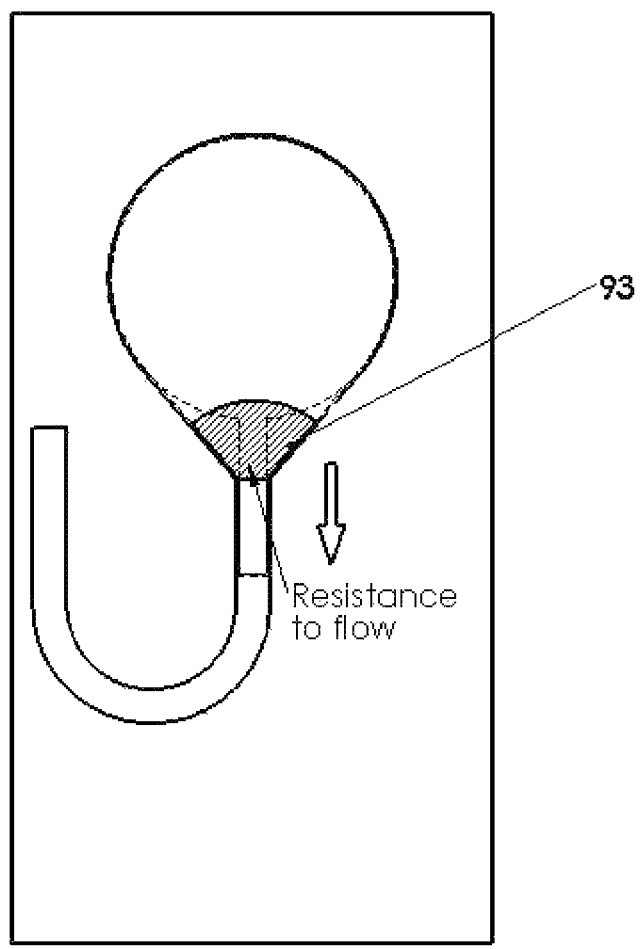
Figure 11:
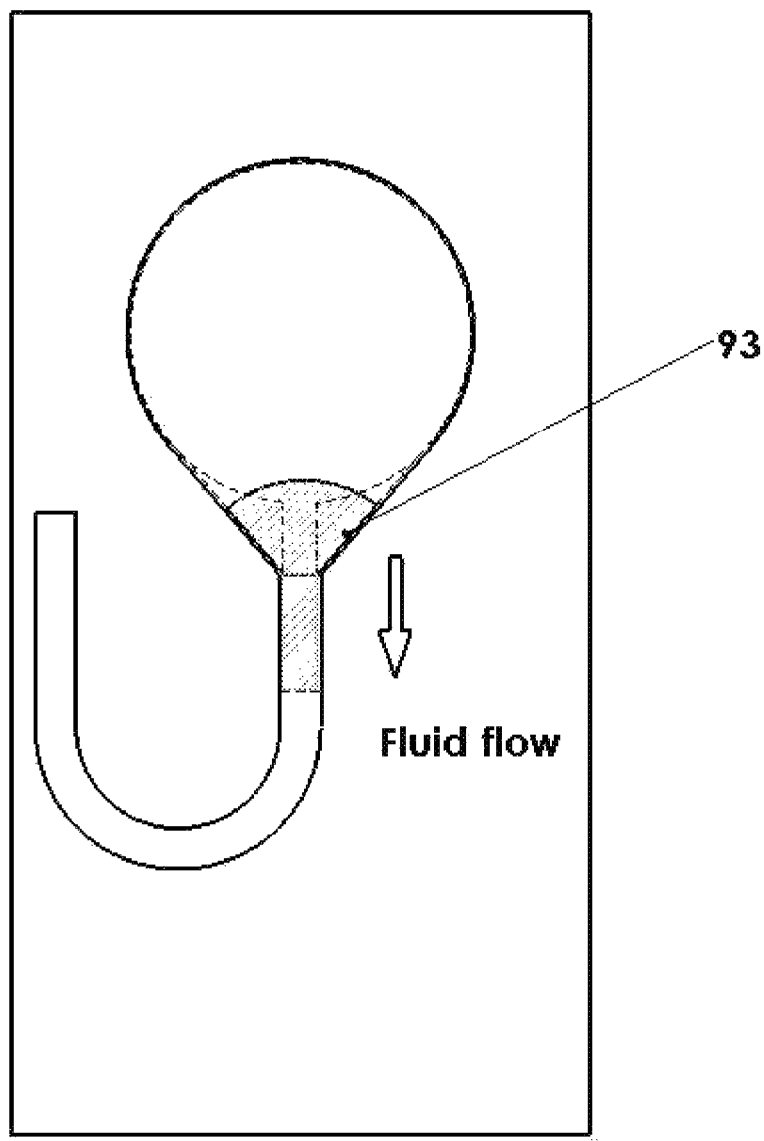
Figure 12:
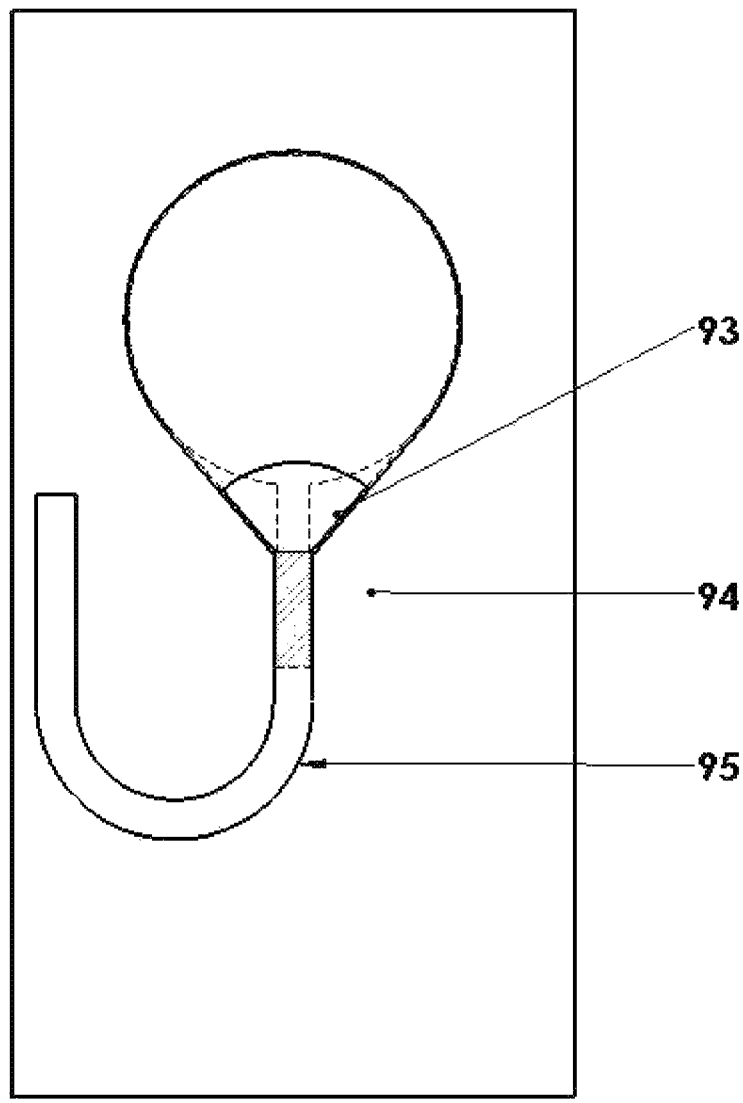

FIGS. 7 and 8 show a final cover plate 70 which is secured over the cover sheet 50. The cover plate 70, which is often formed of a transparent material, is flat and securable by means of the apertures 74 which allow a fixing means to be passed therethrough. One side of the cover plate 70 is, to a greater extent, covered by, or in some embodiments formed from, a hydrophilic material which causes exhaled breath impacting and condensing thereon to form a film. The cover plate 70 is secured to the other elements of the cartridge described above such that the hydrophilic surface faces towards the aperture 44, 54 and the flow of breath from the user.

In use, in this embodiment, the cover plate 70 functions as the condenser plate and so will be, in the finally assembled device, in operable connection with the cooling means. The portion 71 of the cover plate 70 which lies within the apertures 41, 51 is therefore cooled down acting as a heat sink to exhaled breath impacting thereon and causing it to condense into the liquid phase.

As can be seen from FIG. 8, in the region of the outlet from the portion 71 to the sensing zone, the material from which the base card 40 is formed extends beyond that of the cover sheet 50 in the generally triangular sections 45, 46. The triangular sections 45, 46 combine with the surface of the condenser plate 70 and the walls of the apertures 41, 51 to form a capillary tube which acts to draw excess liquid away from the sensing zone and so provide the correct volume within the sensing zone. The distance of the triangular sections from the condensation zone is preferably from 125-350 μm and especially preferably from 250-300 μm to provide good capillary effects.

Preferably, the lip includes a narrow strip whose first end is adjacent to or contiguous with the analysis chamber. The width of the strip is preferably from 125-400 μm, and particularly preferably 125-300 μm.

With regard to FIGS. 9-12, these illustrate a cartridge 90 operating in accordance with a second embodiment of the invention to provide the required volume of liquid in the analysis zone. The second embodiment operates similarly to the first embodiment of the invention in that the surface of the condenser plate 91 is such that the condensed breath forms a film upon the surface. Moreover, the device is provided with lips 92, thin strips 93 and other features indicated to ensure that the correct volume of liquid is within the analysis region, for an accurate measurement to be made.

The hydrophilic material is selected in the second embodiment to provide a higher contact angle with the condensed breath of from 23.0-35.0° and preferably 24.0-26.0° and further preferably 25.0°. A typical class of compounds which can be used are polyesters. This causes the condensed breath to be initially inhibited from flowing from the condenser plate 91 into the analysis region 94 and to build up on the plate 91.

Although the condensed breath still forms a film on the surface of the hydrophilic material, once a critical mass has built up however, this results in the film collapsing and the liquid flowing into the analysis region 94. Because the liquid flows quickly, there would be a reduced opportunity for the air in the analysis region 94 to escape towards the condenser plate 91 and the air would resist the inflow of liquid as it enters the analysis region 94. An air-vent 95 is therefore provided, which air-vent has a diameter insufficient for flow of liquid therethrough. The air-vent 95 comprises a channel of dimensions 3×0.12 mm across with a length of 0.2 mm, leading to an exit area having dimensions 4×0.45 mm and length 3 mm. As the liquid therefore enters the analysis region 94, the air exits via the air-vent as shown by arrow A in FIG. 11. The analysis region 94 is therefore completely filled with no air pockets, and any excess liquid is wicked away by the thin strips 93 and lips 92.

The invention claimed is:

1. A breath-condensate analysis cartridge suitable for incorporation into an exhalation device, the cartridge comprising;
  a condensation zone to receive exhaled breath, the condensation zone having a peripheral region;
  an analysis chamber in which a sample is analyzed;
  a surface of the condensation zone acting to create a fluid flow path in the peripheral region;
  the condensation zone being linked to the analysis chamber by a fluid flow path through the peripheral region;
  a lip to at least partially cover the peripheral region, the lip co-operating with the condensation zone to form a capillary to control fluid flow,
  wherein the condensation zone is coated or formed of a hydrophilic material.

2. The cartridge according to claim 1, wherein the condensation zone is circular.

3. The cartridge according to claim 2, wherein the condensation zone has a diameter of from 15.0-25.0 mm.

4. The cartridge according to claim 3, wherein the diameter is 20.0 mm.

5. The cartridge according to claim 1, wherein a hydrophilicity of the surface of the condensation zone is selected to be such as to form an angle with breath condensate of less than 20.0°.

6. The cartridge according to claim 5, wherein the angle is from 5.0°-15.0°.

7. The cartridge according to claim 1, wherein the analysis chamber includes an air-vent and a hydrophilicity of the surface of the condensation zone is selected to be such as to form an angle with breath condensate of less than 23.0°-35.0°.

8. The cartridge according to claim 7, wherein the angle is selected to be from 24.0°-26.0°.

9. The cartridge according to claim 1, wherein the lip includes a strip whose first end is adjacent or contiguous the analysis chamber.

10. The cartridge according to claim 9, wherein a width of the strip is from 125-400 μm.

11. The cartridge according to claim 10, wherein the width of the strip is from 125-300 μm.

12. The cartridge according to claim 9, wherein a distance of the strip from the condensation zone is from 125-350 μm.

13. The cartridge according to claim 12, wherein the distance is 250-300 μm.

14. The cartridge according to claim 1, wherein a portion of the condensation zone is formed of or coated with a hydrophobic material, the portion being located adjacent the analysis chamber and the peripheral region.

15. The cartridge according to claim 1, wherein the cartridge has a laminar structure which aids in allowing the cartridge to bend.

\* \* \* \* \*